United States Patent [19]

Bartner

[11] 4,394,863
[45] Jul. 26, 1983

[54] AUTOMATIC INJECTOR WITH CARTRIDGE HAVING SEPARATE SEQUENTIALLY INJECTABLE MEDICAMENTS

[75] Inventor: Elliot Bartner, Piscataway, N.J.

[73] Assignee: Survival Technology, Inc., Bethesda, Md.

[21] Appl. No.: 314,381

[22] Filed: Oct. 23, 1981

[51] Int. Cl.³ .............................................. A61M 5/00
[52] U.S. Cl. ...................................................... 604/90
[58] Field of Search ........... 128/218 R, 218 A, 218 C, 128/218 F, 218 D, 218 DA, 218 P, 213, 215, 216, 234

[56] References Cited

U.S. PATENT DOCUMENTS

| | | | |
|---|---|---|---|
| 1,943,120 | 1/1934 | Kabnick | 128/218 |
| 2,591,046 | 4/1952 | Brown | 128/218 |
| 2,832,339 | 4/1958 | Sarnoff | 128/218 |
| 3,326,215 | 6/1967 | Sarnoff | 128/218 |
| 3,330,282 | 7/1967 | Visser | 128/272 |
| 3,380,449 | 4/1968 | Sarnoff | 128/218 |
| 3,391,695 | 7/1968 | Sarnoff | 128/218 |
| 3,424,155 | 1/1969 | Sarnoff | 128/218 |
| 3,494,359 | 2/1970 | Zackheim | 128/218 |
| 3,572,336 | 3/1971 | Hershberg | 128/218 |
| 3,712,301 | 1/1973 | Sarnoff | 128/218 |
| 3,882,863 | 5/1975 | Sarnoff | 128/218 |
| 3,911,916 | 10/1975 | Stevens | 128/218 R |
| 4,031,893 | 6/1977 | Kaplan | 128/218 |
| 4,226,235 | 10/1980 | Sarnoff | 128/218 |

Primary Examiner—John D. Yasko
Attorney, Agent, or Firm—Cushman, Darby & Cushman

[57] ABSTRACT

An automatic injector comprising an elongated housing assembly having a forward end, a stressed spring assembly mounted within the rearward end of the housing assembly so as to be released in response to a predetermined manual actuation procedure, and a medicament injection cartridge assembly mounted within the forward end of the housing assembly in cooperating relation with the stressed spring assembly. The improvement of the present invention is in the medicament injection cartridge assembly which includes a medicament container, a hypodermic needle disposed forwardly of the container mounted in a sterile condition within the housing assembly adjacent the forward end thereof. A forward seal is provided for sealing the forward end of the container from the hypodermic needle. A rearward piston is mounted in the rearward end of the container for forward movement therein in slidably sealed relation thereto. A plurality of individual dosages of different relatively incompatible liquid medicaments is disposed within the container between the forward seal and the piston separated by a movable interior seal within the interior of the container between the piston and the forward seal. The improved arrangement is operable in response to the manual accomplishment of the manual actuating procedure and the resultant release of the stressed spring assembly to move the hypodermic needle forwardly and outwardly of the housing assembly into the muscle tissue of a patient and the piston forwardly into the container so that the plurality of individual dosages therein is moved forwardly out of sealed relation with respect to the forward and interior seal outwardly through the needle into the muscle tissue of the patient.

5 Claims, 4 Drawing Figures

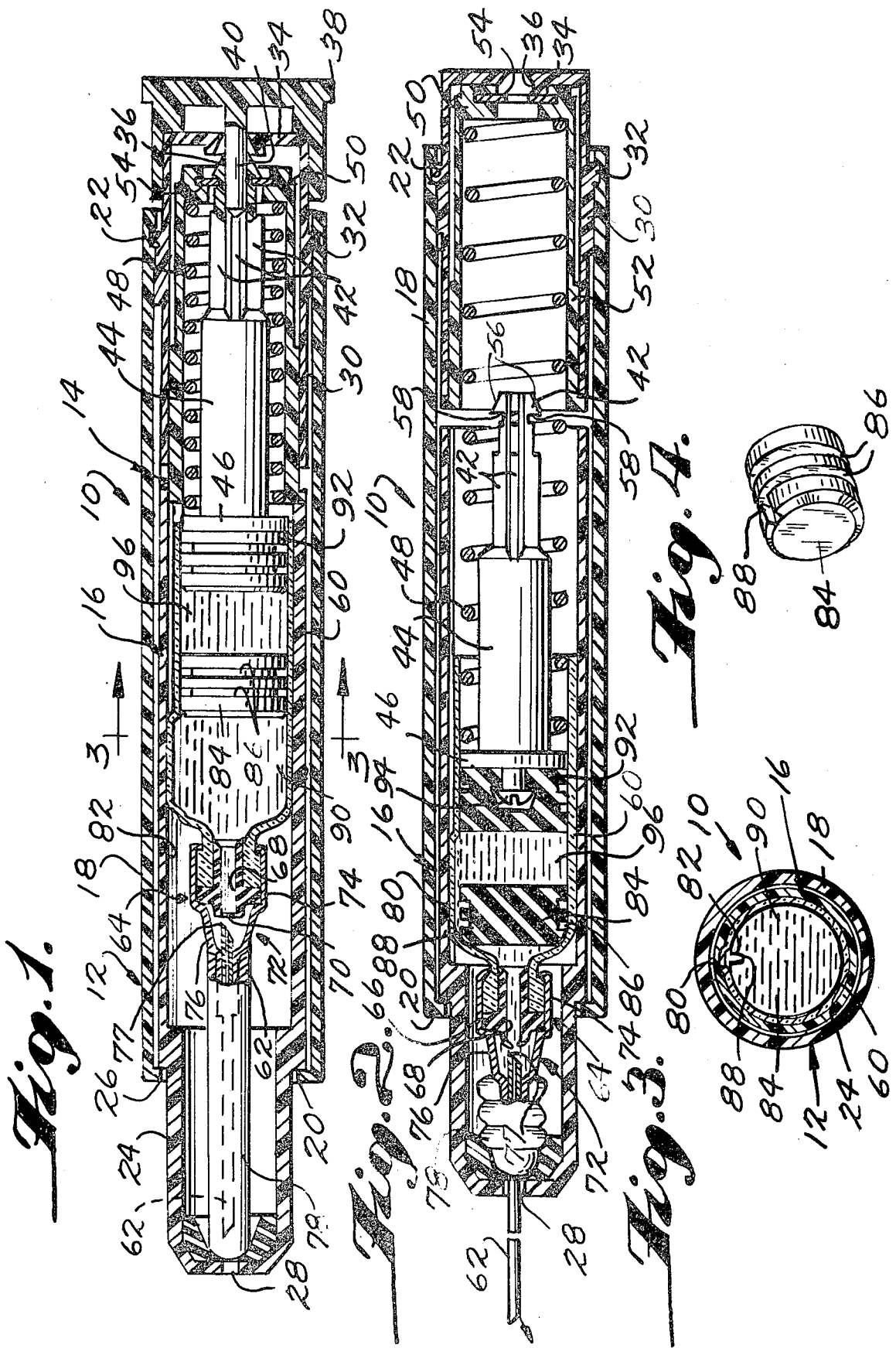

AUTOMATIC INJECTOR WITH CARTRIDGE HAVING SEPARATE SEQUENTIALLY INJECTABLE MEDICAMENTS

This invention relates to the injection of medicaments and more particularly to improvements in injection devices of the type in which the insertion of the hypodermic needle and injection of the medicament dosage through the inserted needle are both accomplished automatically by a spring force in response to a simple actuation procedure.

It has long been recognized that there are many situations where an individual must self-inject a medicament dosage where it is not practical to provide the individual with the same syringe type of injection equipment normally utilized by professionals to inject others. It is well known that many individuals have great difficulty in performing the act of pushing a hypodermic needle into one's own flesh. To enable self injection to become a simpler, more viable procedure, so-called "automatic injectors" have been developed. Basically, injectors of the automatic type provide for the storage of a medicament dosage and hypodermic needle within a housing in operative relation with a cocked or stressed spring. The stressed spring is controlled by a releasing mechanism which, when actuated, serves to release the stressed spring, thereby releasing a force sufficient to move the hypodermic needle outwardly and the medicament dosage outwardly through the needle. A safety device is provided for preventing an unwanted actuation of the spring releasing mechanism, thus insuring that actuation will take place only after a deliberate actuating procedure has been accomplished including an appropriate interengagement of the device with the muscle tissue to be injected.

Examples of automatic injectors which have been heretofore available for the injection of nerve gas antidotes and cardiac arrhythmia dosages under emergency conditions are U.S. Pat. Nos. 2,832,339; 3,712,301; and 3,882,863.

The present invention relates to the provision of automatic injectors which have the capability of injecting a plurality of individual medicament dosages. This capability has been dealt with in the prior patented literature. An early example is contained in U.S. Pat. No. 3,572,336. The patent contemplates the automatic injection of a plurality of drugs through a plurality of needles simultaneously or where the drugs are slightly incompatible, they can be mixed prior to injection into the patient through a single needle. In both instances, however, the plural capability is obtained by simply providing a plurality of parallel dosage receiving chambers and directing the dosages either to a common needle or separate needles. In both instances the discharge of the plural dosages is simultaneously accomplished by moving interconnected plungers through the chambers in a single dosage discharging stroke by a single spring.

In commonly assigned U.S. Pat. No. 4,226,235, there is disclosed an improvement upon the simple plural arrangement of the earlier patent in which advantages are attributable to the use of plural injectors having the capability of insuring simultaneous or substantially simultaneous sequential actuation. The advantages obtained as a result of the improvements disclosed in the later patent accrue largely in situations where one of the plural dosages is of the type which is likely to be changed in the future.

There are many other situations presented in which it is desirable to provide for the injection of plural dosages and yet which do not warrant the costs involved in pluralizing the automatic injector structure. For example, in nerve gas antidote injectors, a dosage of atropine and pralidoxime chloride, both of which are soluble in water, can be desirably coupled with a dosage of Valium which is not water soluble and requires a propylene glycol solution. Basically, the Valium is an adjuct in nerve gas therapy. Consequently, there exists a need for an automatic injector which can simply and economically accommodate an additional separate incompatible liquid medicament for effective injection together with the one already provided in accordance with usual manual procedure for effecting automatic operation.

It is an object of the present invention to fulfill the aforesaid need. In accordance with the principles of the present invention this objective is obtained by providing an automatic injecting device which includes the usual three basic components of an elongated housing assembly having a forward end, a stressed spring assembly mounted within the rearward end of the housing assembly so as to be released in response to a predetermined manual actuation procedure, and a medicament injection cartridge assembly mounted within the forward end of the housing assembly in cooperating relation with the stressed spring assembly. The improvement of the present invention is in the medicament injection cartridge assembly. In accordance with the principles of the present invention the improved cartridge assembly includes a medicament container, a hypodermic needle disposed forwardly of the container mounted in a sterile condition within the housing assembly adjacent the forward end thereof. A forward seal is provided for sealing the forward end of the container from the hypodermic needle. A rearward piston is mounted in the rearward end of the container for forward movement therein in slidably sealed relation thereto. A plurality of individual dosages of different relatively incompatible liquid medicaments is disposed within the container between the forward seal and the piston separated by a movable interior seal within the interior of the container between the piston and the forward seal. Finally, means is provided which is operable in response to the manual accomplishment of the manual actuating procedure and the resultant release of the stressed spring assembly for moving the hypodermic needle forwardly and outwardly of the housing assembly into the muscle tissue of a patient and the piston forwardly into the container so that the plurality of individual dosages therein is moved forwardly out of sealed relation with respect to the forward and interior seal outwardly through the needle into the muscle tissue of the patient.

In terms of the simplicity embodied in the present invention, reference is made to commonly assigned U.S. Pat. No. 4,031,893. This patent discloses an automatic injector which has been commercially manufactured under the trademark ComboPen ® which provides an injection cartridge in which the amount of medicament contained within the cartridge is varied by the provision of a spacer member within the cartridge container rearwardly of the piston thereof. The present invention contemplates the utilization of the space taken up by the spacer within the cartridge to contain the second medicament. The other modifications to the structure required to obtain the present objectives can likewise be simply and economically effected.

An important advantage of the present invention is that applicant has ascertained that the manual actuating procedure responsive means described above can take a form similar to the structures heretofore provided in manually actuated syringes for mixing two separate medicament ingredients, usually a powder and a soluent. Examples of prior art structures of this type are included in the following patents: U.S. Pat. Nos. 1,943,120; 2,591,046; 3,326,215; 3,330,282; and 3,494,359. In all of these mixing devices of the prior art, the structure provided requires a preliminary manual manipulation through which the separately retained ingredients are communicated, a subsequent intermixing by manual shaking and, finally, a manual injection. As far as applicant is aware, structures of this type have never been utilized in automatic injectors where a spring force is utilized to effect injection, presumably because of the need for sequential manual procedures in the operation thereof. In its broadest aspects the present invention contemplates the utilization of any of the prior art mixing arrangements. However, in the preferred embodiment sequential injection of plural separately retained liquid medicaments is achieved by providing a by-pass bulge in the peripheral wall of the cartridge container. In order to insure sequential injection of a maximum amount of the liquid retained in the cartridge it is preferable to provide an intermediate piston having an axial groove in the periphery thereof which communicates with a forward peripheral groove in the piston.

Another object of the present invention is the provision of an automatic injector with an improved cartridge having separate sequentially injectable medicaments which is simple in construction, effective in operation and economical to manufacture and maintain.

These and other objects of the present invention will become more apparent during the course of the following detailed description and appended claims.

The invention may best be understood with reference to the accompanying drawings, wherein an illustrative embodiment is shown.

In the drawings:

FIG. 1 is a longitudinal sequential view of an automatic injector embodying the principles of the present invention showing the same in its normal storage position;

FIG. 2 is a view similar to FIG. 1 showing the position of the parts just prior to the completion of the injection operation;

FIG. 3 is a sequential view taken along the line 3—3 of FIG. 1; and

FIG. 4 is a perspective view of the intermediate piston constructed in accordance with the principles of the present invention.

Referring now more particularly to the drawings, there is shown therein an automatic injector, generally indicated at 10, which embodies the improvements of the present invention. The injector consists essentially of three basic assemblies: one, a housing assembly, generally indicated at 12; two, a power pack or stressed spring assembly, generally indicated at 14, mounted within the rearward end portion of the housing assembly 12 and operable in response to a predetermined manual actuating procedure to be released so as to operate the third assembly, which is a medicament injection cartridge assembly, generally indicated at 16, embodying the improvements of the present invention. While the housing assembly 12 and stressed spring assembly 14 can assume any known configuration, the preferred embodiment as shown is constructed in accordance with the teachings contained in U.S. Pat. Nos. 3,712,301 and 3,882,863, which disclosures are hereby incorporated by reference into the present specification.

As best shown in FIGS. 1 and 2, the housing assembly 12 includes an outer tubular member 18 having a radially inwardly turned flange 20 on the forward end thereof and an interior annular groove 22 in the rearward end thereof. The housing assembly 12 also includes an inner tubular member 24 having a forward end portion of reduced diameter defining an exterior forwardly facing shoulder 26 which is adapted to engage the forward flange 20 of the outer tubular member 18 when the inner tubular member is disposed therein in operative position. The inner tubular member 24 includes a forward end having a needle opening 28 therein and the interior of the inner tubular member is configured to receive the cartridge assembly 16.

The stressed spring assembly 14 as preassembled includes an outer tubular member 30 having an annular ridge 32 formed on the exterior periphery thereof adjacent the rearward end portion which serves to engage within the annular groove 22 of the outer tubular member 18 when the injector is assembled in operative position, as shown in FIG. 1. The outer tubular member 30 includes a rearward end wall 34 having a central opening therein defined by a frustoconical surface 36 which diverges inwardly. The stressed spring assembly includes a safety cap 38 which detachably fits over the portion of the outer member 30 extending rearwardly from the outer tubular member 18. The safety cap 38 includes a central inwardly extending safety pin 40 which in its normal preassembly position extends through and inwardly of the frustoconical surface 36.

The safety pin 40 is adapted to cooperate with a plurality of spring fingers 42 extending from the rear end of a plunger 44 having an annular flange 46 extending rearwardly outwardly from the forward end thereof. The rearward surface of the flange 46 is adapted to engage one end of a stressed coil spring 48, the other end of which engages an apertured rear wall 50 of a tubular member 52 slidably mounted within the tubular member 30. The apertured end wall 50 has formed therein an apertured catch plate or disc 54. The central opening of the catch plate 54 is of a size to engage inclined surfaces 56 formed on the outer rearward portions of the spring fingers 42 so as to deflect the fingers radially inwardly as the rearward ends of the fingers pass rearwardly therethrough. Each spring finger 42 has formed therein an exterior catch receiving notch 58 which is adapted to receive the catch plate 54 when the spring fingers have been moved rearwardly through the catch plate into the normal spring stressed preassembly position, as shown in FIG. 1. In this regard it will be noted that safety pin 40 engages within the inner surfaces of the spring fingers 42 and hence prevents their radially inward movement so that the tubular members 30 and 52, plunger 44 and safety cap 38 can be preassembled and mounted in operative position within the outer tubular member 18 as a unit. In the operative position, the members 30 and 52 of the power pack assembly 14 may be regarded as part of the housing assembly 12. Preferably, members 30 and 52, as well as members 18 and 24, are made of a suitable plastic material, as is indicated in the aforesaid patents.

The cartridge assembly 16 which is constructed in accordance with the principles of the present invention includes a medicament container 60 which, as shown, is preferably made of glass and is essentially in the form of a necked bottomless bottle having a substantially cylindrical peripheral wall. The cartridge assembly also includes a hypodermic needle 62 which is disposed forwardly of the container 60 and has its rearward end connected with the necked end of the container 60 by a connecting assembly, generally indicated at 64. The connecting assembly 64 is preferably constructed in accordance with the teachings contained in commonly assigned U.S. Pat. No. 3,380,449 (see also U.S. Pat. Nos. 3,391,695 and 3,424,155), the disclosures of all of which are hereby incorporated by reference into the present specification. As shown, the assembly 64 includes a resilient stopper 66 engaged within the necked end of the container 60, the stopper providing a central passage 68 which leads to an exterior integral resilient diaphragm seal 70. Disposed in exterior engagement with the stopper 66 is a fitting 72. A rearward sleeve portion 74 of the fitting 72 is engaged over the forward marginal and outer periphery of the stopper 76 and the neck portion of the container 60 and has its rearward end turned down to effectively secure the components of the assembly in operative position. A reduced forward end portion 76 of the fitting 72 fixedly receives a portion of the hypodermic needle 62 spaced slightly from the rearward end thereof. As shown, the rearward end of the hypodermic needle is sharpened, as indicated at 77, and positioned in forwardly spaced relation from the seal 70.

In accordance with the principles set forth in U.S. Pat. No. 3,882,863, the remaining forwardly extending portion of the hypodermic needle 62 is encased within a rubber sheath 78 which serves the dual function of maintaining the needle in a sterile condition when the injector 10 is in its storage condition and to provide a shock absorbing effect during the injection procedure, all in accordance with the teachings set forth in the aforesaid patent.

In accordance with the principles of the present invention, the peripheral wall of the container 16 which is otherwise cylindrical includes an axially extending radially outward bulge 80. While it is within the contemplation of the present invention to simply provide a cylindrical interior surface within the interior tubular member 24 to longitudinally slidably receive the container 60 therein, as shown the interior periphery has formed therein an axial groove 80 of a shape to accommodate the bulge 80. Mounted within the central portion of the container 60 in a position rearwardly of the bulge 80 is an interior seal in the form of an intermediate piston 84. As best shown in FIG. 4, the intermediate piston 84 is preferably made of soft rubber and has formed in the exterior periphery thereof a pair of axially spaced forward and rearward annular grooves 86. Extending between the forward annular groove 86 and the forward face of the intermediate piston 84 is an axial groove 88 which is provided for a purpose hereinafter to be more fully described.

The cartridge assembly 16 also includes a first liquid medicament 90 within the container 60 between the forward seal provided by the diaphragm 70 and the interior seal provided by the intermediate piston 84. As previously stated, an exemplary medicament is a mixture of atropine and pam in a water solvent which is used as an anti-nerve gas antidote.

Mounted within the rear open end of the container 60 is a rearward piston 92. This piston is similar in construction to the piston 84 except that it has a hollow interior configured to receive a central projection 94 extending forwardly from the plunger 44 so as to provide an interconnection between the same. Finally, the cartridge assembly 16 includes a second relatively incompatible liquid medicament 96 disposed within the container 60 between the interior seal provided by the intermediate piston 84 and the rear seal provided by the rearward piston 92. An exemplary medicament 96 is Valium contained within a propylene glycol solvent.

OPERATION

FIG. 1 illustrates the assembled storage position of the automatic injector 10 and it will be noted that the stressed spring assembly 14 includes the assembled safety cap 38 which serves to prevent the spring fingers from moving radially inward to release the stressed spring. The cartridge assembly 16 is mounted forwardly within the housing assembly 12 in cooperating relation with the stressed spring assembly 14. As previously indicated, the forward and rearward liquid medicaments are sealed within the container 60 in the manner previously indicated. When it is desired to inject the medicaments, the safety cap 38 is initially removed, thus displacing the safety pin 40 from its storage position within the spring fingers and hence permitting the same to move radially inwardly.

The actuation procedure consists in the patient manually gripping the exterior periphery of the outer tubular member 18 and then moving the injector forwardly into contact with the muscle tissue to be injected, as for example, a thigh. When the forward end of the inner member 18 engages the exterior of the thigh, continued forward movement exerted on the exterior periphery of the outer member results in a relative longitudinal movement between rear end walls 50 and 34, causing the frustoconical surface 36 to engage the spring finger surfaces 56 and thus move the same radially inwardly by a camming action so as to disengage the grooves 58 from the catch plate, thus releasing the stressed spring 48. As the stressed spring 48 is released the entire cartridge assembly 16 is moved forwardly within the housing assembly 12 during which time the forward pointed end of the hypodermic needle 62 moves outwardly through the sheath 78 and opening 28 and into the muscle tissue of the patient. Rubber sheath 78 is compressed during this movement and this compression serves to retard the final forward movement of the cartridge with a shock absorbing effect. As the forward movement of the container 60 and needle 62 is retarded, the released stressed spring 48 continues to move the plunger 44 forward which carries with it the rearward piston 92. The adjacent rearward liquid medicament 96 within the container 60 is placed under pressure in response to the initial movement of the rear piston 92. The pressurized liquid medicament 96 transmits the movement of the rearward piston 92 to the intermediate piston 84, thus pressurizing the forward liquid medicament 90, causing the diaphragm 70 sealing the forward end of the liquid medicament 90 to bulge forwardly. In the event that this bulging movement does not serve to burst the diaphragm 90 prior to the engagement with the sharpened rear end 77 of the hypodermic needle 62, the engagement with the sharpened rear end 77 insures that the diaphragm 70 will burst, allowing the pressurized liquid medicament 90 in pressure communication therewith to pass into the forward portion 76 of the fitting 72 and forwardly through the hypodermic needle 62 outwardly into the muscle tissue of the patient.

Movement of the forward liquid medicament 90 outwardly through the hypodermic needle 62 will continue until the forward movement of the intermediate piston 84 is retarded by engagement of the forward surface thereof with the necked forward end of the container 60. It will be noted, however, that the axial extent of the bulge 80 is greater than the axial thickness of the intermediate piston 84 so that when the intermediate piston reaches the forward necked end of the container, the bulge 80 provides a bypass for the flow of the rearward liquid medicament 96 forwardly from a position rearwardly of the rear surface of the intermediate piston to a position forwardly of the forward surface thereof. The axial peripheral groove 88 in the piston 84 insures that there will always be a flow path from the bypassing rearward liquid medicament 96 to the stopper passage 68 and hypodermic needle 62 as the rearward piston 92 continues its forward movement under the bias of the released stressed spring 48.

FIG. 2 illustrates the position of the parts just after forward movement of the intermediate piston 84 has been halted. During the remainder of the forward movement of the rearward piston 92, the rearward liquid medicament 96 is forced outwardly through the bypass provided by the bulge 80 and piston groove 88 and outwardly through the hypodermic needle 62 into the muscle tissue of the patient. It will be noted that when the forward surface of the rearward piston engages the rearward surface of the intermediate piston, the rearward peripheral portion of the piston 92 has not yet reached the bulge 80.

It will be understood that the above-described operation of the automatic injector 10 takes place quite rapidly so that insofar as the patient is concerned the operation occurs so rapidly after the actuating procedure has been performed as to require the operator simply to withdraw the needle after a few seconds have elapsed. It can thus be seen that by the improvements embodied in the cartridge assembly of the present invention it becomes possible to effectively independently store a plurality of relatively incompatible liquid medicaments within an automatic injector and to effectively sequentially inject the liquid medicaments in a conventional automatic fashion by an arrangement which is economical in the simplicity of the improvements provided when compared with an automatic injector having a conventional single dosage cartridge assembly.

It thus will be seen that the objects of this invention have been fully and effectively accomplished. It will be realized, however, that the foregoing preferred specific embodiment has been shown and described for the purpose of illustrating the functional and structural principles of this invention and is subject to change without departure from such principles. Therefore, this invention includes all modifications encompassed within the spirit and scope of the following claims.

What is claimed is:

1. In an automatic injecting device including an elongated housing assembly having a forward end, stressed spring means mounted within said housing so as to be released in response to a predetermined manual actuation procedure, and a medicament injection cartridge assembly mounted within said housing assembly in co-operating relation with said stressed spring means, the improvement which comprises said medicament injection cartridge assembly comprising a medicament container, a hypodermic needle disposed forwardly of said container mounted in a sterile condition within said housing assembly adjacent the forward end thereof, forward seaing means for sealing the forward end of said container from said hypodermic needle, a rearward piston mounted in the rearward end of said container for forward movement therein in slidably sealed relation thereto, a plurality of individual dosages of different relatively incompatible liquid medicaments within said container between said forward sealing means and said piston, said plurality of dosages including a forward dosage and a rearward dosage, movable interior sealing means within the interior of said container between said piston and said forward sealing means maintaining the individual dosages sealingly separated from one another, said interior sealing means comprising an intermediate piston between said forward and rearward dosages mounted for forward movement within said container in slidably sealed relation thereto, means operable in response to the manual accomplishment of said manual actuating procedure and the resultant release of said stressed spring means for moving said hypodermic needle forwardly and outwardly of said housing assembly into the muscle tissue of a patient and said piston forwardly into said container so that the plurality of individual dosages therein are moved forwardly out of sealed relation with respect to said forward and interior sealing means outwardly through said needle into the muscle tissue of the patient, said manual actuating procedure responsive means comprising a by-pass bulge in the peripheral wall of said container adjacent the forward end thereof of an axial extent sufficient to enable the forward movement of said rearward dosage to move said intermediate piston forwardly into a by-pass position adjacent the forward end of said container during which said forward dosage is moved forwardly and outwardly through said needle and following which the forward movement of the rearward dosage continues through said by-pass bulge and outwardly through said needle.

2. The improvement as defined in claim 1 wherein said intermediate piston includes a generally cylindrical body of resilient material having a pair of axially spaced forward and rearward annular grooves formed in the exterior periphery thereof, said manual actuating procedure responsive means further including an axial groove formed in the periphery of said cylindrical piston body between the forward annular groove thereof and the forward end surface thereof.

3. The improvement as defined in claim 2 wherein said housing assembly includes a tubular housing member within which said container is mounted for forward sliding movement, said tubular housing member including an axial groove in the interior periphery thereof for receiving said by-pass bulge.

4. The improvement as defined in claim 1, 2 or 3 wherein said forward sealing means comprises a resilient burstable diaphragm disposed in the forward end of said container so as to be flexed forwardly in response to an increase in pressure in the liquid medicament contacting the same, said manual actuating procedure responsive means including piercing edge means disposed forwardly adjacent said diaphragm for insuring that the forward flexure of said diaphragm will result in the bursting of the same.

5. In an automatic injecting device including an elongated housing assembly having a forward end, stressed spring means mounted within said housing assembly so as to be released in response to a predetermined manual actuation procedure, and a medicament injection cartridge assembly mounted within said housing assembly in cooperating relation with said stressed spring means, the improvement which comprises said medicament injection cartridge assembly comprising:

a medicament container, a hypodermic needle disposed forwardly of said container mounted in a sterile condition within said housing assembly adjacent the forward end thereof, forward burstable sealing means for sealing the forward end of said container from said hypodermic needle, a rearward piston mounted in the rearward end of said container for forward movement therein in slidably sealed relation thereto, forward and rearward individual dosages of different relatively incompatible liquid medicaments within said container between said forward sealing means and said piston, movable intermediate sealing means within the interior of said container between said piston and said forward sealing means maintaining the individual dosages sealingly separated from one another, means operable in response to the manual accomplishment of said manual actuating procedure and the resultant release of said stressed spring means for moving said piston forwardly and hence initially the entire cartridge assembly therewith including the hypodermic needle forwardly and outwardly of said housing assembly into the muscle tissue of a patient, means operable in response to the arresting of the forward movement of the container of said assembly when said needle has been moved into the muscle tissue of a patient and the continued forward movement of said piston within said container for causing said forward burstable sealing means to burst releasing said forward dosage for movement outwardly of said needle by virtue of the forward movement of said intermediate sealing means with respect to said container, and means operable in response to the forward movement of said intermediate sealing means toward and into a forward limiting position within said container and the continued forward movement of said piston within said container for causing the rearward dosage to move out of sealed relation with said intermediate sealing means and into communication with said needle for movement outwardly thereof in response to the continued forward movement of said piston.

* * * * *